United States Patent

Huitema et al.

[11] Patent Number: 5,823,066
[45] Date of Patent: Oct. 20, 1998

[54] ARTICULATION TRANSMISSION MECHANISM FOR SURGICAL INSTRUMENTS

[75] Inventors: Thomas Huitema, Cincinnati; Richard P. Nuchols, Loveland; Bryan D. Knodel, Cincinnati, all of Ohio

[73] Assignee: Ethicon Endo-Surgery, Inc., Cincinnati, Ohio

[21] Appl. No.: 645,434

[22] Filed: May 13, 1996

[51] Int. Cl.[6] .................................................. G05G 5/06
[52] U.S. Cl. ........................... 74/527; 74/528; 606/143; 606/142; 227/175.1; 128/751
[58] Field of Search .................. 74/527, 528, 530, 74/543, 545; 606/143, 142; 227/175.1, 177.1, 19, 176.1, 178.1, 179.1, 180.1; 128/751

[56] References Cited

U.S. PATENT DOCUMENTS

| | | | |
|---|---|---|---|
| 3,525,272 | 8/1970 | Olson | 74/528 X |
| 4,728,020 | 3/1988 | Green et al. | 227/19 |
| 4,770,057 | 9/1988 | Foggini | 74/523 |
| 4,869,414 | 9/1989 | Green et al. | 227/19 |
| 5,213,004 | 5/1993 | Hobringre | 74/493 |
| 5,257,999 | 11/1993 | Slantez | 606/147 |
| 5,312,023 | 5/1994 | Green et al. | 227/175 |
| 5,326,013 | 7/1994 | Green et al. | 227/176 |
| 5,330,502 | 7/1994 | Hassler et al. | 606/205 |
| 5,374,277 | 12/1994 | Hassler | 606/207 |
| 5,381,943 | 1/1995 | Allen et al. | 227/177 |
| 5,383,888 | 1/1995 | Zvenyatsky et al. | 606/206 |
| 5,403,342 | 4/1995 | Tovey et al. | 606/205 |
| 5,405,344 | 4/1995 | Williamson et al. | 606/1 |
| 5,409,498 | 4/1995 | Braddock et al. | 606/143 |
| 5,411,519 | 5/1995 | Tovey et al. | 606/207 |
| 5,417,203 | 5/1995 | Tovey et al. | 128/4 |
| 5,447,513 | 9/1995 | Davison et al. | 606/143 |
| 5,456,684 | 10/1995 | Schmidt et al. | 606/41 |
| 5,626,608 | 5/1997 | Cuny et al. | 606/205 |

FOREIGN PATENT DOCUMENTS 0509969  10/1992  European Pat. Off. .................. 74/528

*Primary Examiner*—Vinh T. Luong
*Attorney, Agent, or Firm*—Matthew S. Goodwin

[57] ABSTRACT

An articulating surgical instrument with an articulation transmission assembly for remotely articulating the end effector of the instrument includes a body with a housing mounted on the instrument, oscillating and rotating members, and an actuator rotatably mounted on the housing and secured to the rotating member. The oscillating member is seated rotationally stationary within the housing. The rotating member fits into the oscillating member, and has a drive shaft extending into the body for translating rotation from the rotating member into reciprocation of an elongated transmission rod attached to the drive shaft. First and second sets of unloading teeth are displayed on the oscillating member and actuator, respectively. First and second locking teeth are displayed on the oscillating and rotating members, respectively. The assembly provides ratcheting rotation for precisely positioning the end effector in discrete positions. In the preferred embodiment, the frictional forces between the unloading teeth are less than those between the locking teeth. The instrument may be used for endoscopic as well as conventional open surgical procedures.

9 Claims, 8 Drawing Sheets

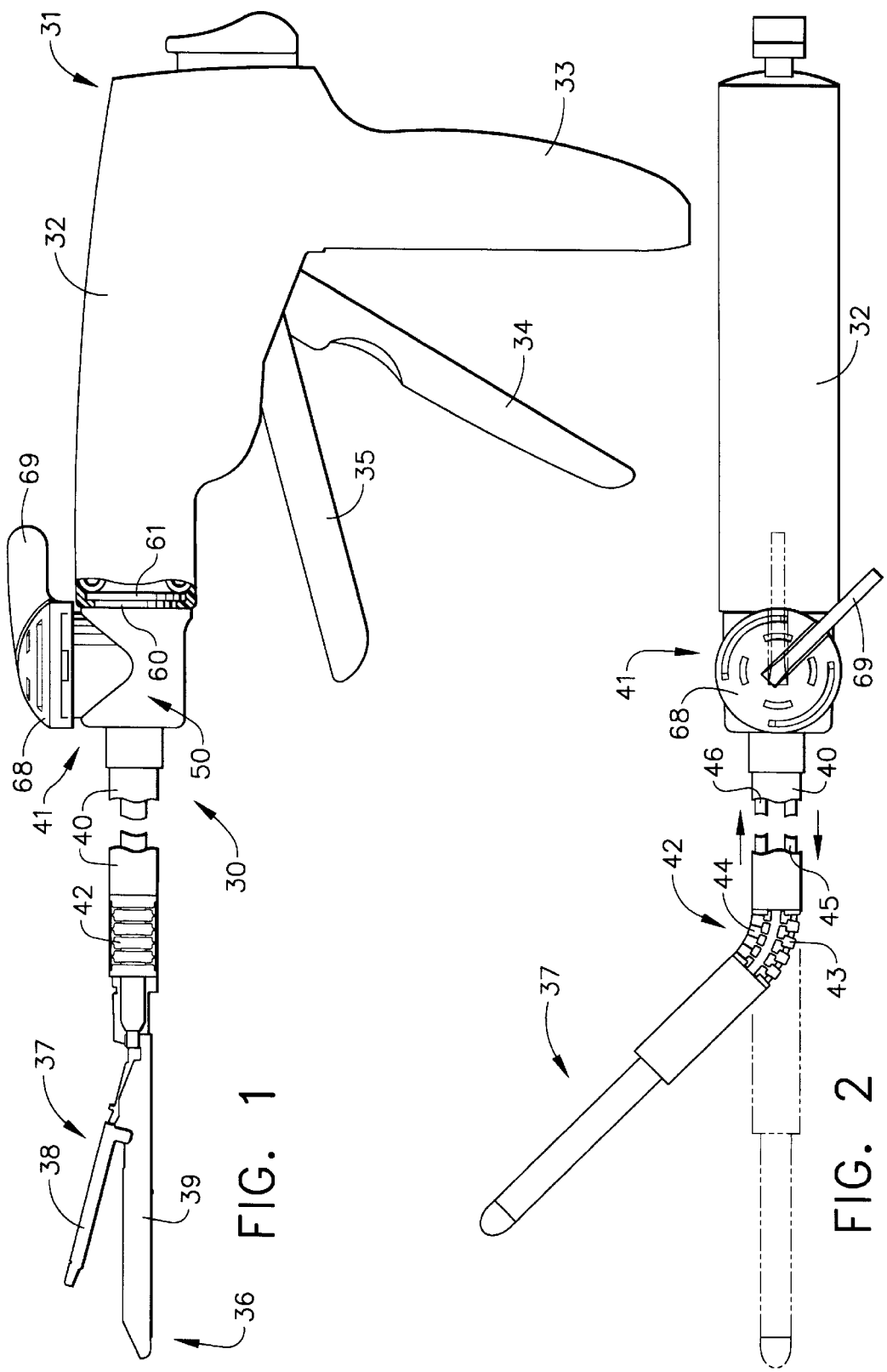

_US005823066A_

ARTICULATION TRANSMISSION MECHANISM FOR SURGICAL INSTRUMENTS

BACKGROUND OF THE INVENTION

This invention relates to surgical instruments for performing various surgical procedures, especially endoscopic surgical procedures. In particular, it relates to the instrument mechanism which allows the surgeon to precisely position the instrument at the endoscopic surgical site conveniently and with a high degree of confidence.

During a surgical procedure, particularly an endoscopic surgical procedure, access to the surgical site within the body cavity may be provided through openings of a small diameter made in the body wall. An instrument frequently used to provide this access is the trocar. The trocar is an assembly which includes an obturator and a cannula. The obturator has a sharp tip which is used to puncture the body wall to provide the access opening. The obturator slides within the cannula, which is a hollow, cylindrical sleeve. When the obturator has punctured the body wall, the obturator is removed from the cannula. The cannula, however, remains in place within the opening made in the body wall by the obturator. Consequently, the cannula provides a cylindrical passageway to gain access to the surgical site within the body cavity.

Accordingly, a characteristic feature of many endoscopic surgical instruments is a long cylindrical shaft which can slide through the trocar cannula. At the business end of the shaft, which is the end of the instrument coming into contact with tissue at the surgical site within the body cavity, an "end effector" is provided to manipulate the tissue in some way to carry out a desired surgical procedure. The business end, including the end effector, must likewise be capable of sliding through the trocar cannula. At the opposite end of the shaft, there is an actuator operatively connected to the business end to remotely control the performance of the end effector. The actuator is conveniently housed in a frame which may include a pistol grip handle with one or more pivoting triggers. Alternatively, the actuator may include a lever, or the combination of a pivoting trigger and a lever. The actuator is activated when the surgeon pivots the trigger or depresses the lever. These actions in turn cause the end effector to perform its desired function.

Before the surgeon can actuate the end effector to manipulate tissue to perform a desired surgical procedure, the end effector must be carefully positioned at the desired location within the endoscopic surgical site. It also must be positioned at a proper orientation if, for example, staples must be fired in a certain direction to properly fasten the tissue. Therefore, endoscopic surgical instruments typically include mechanisms to enable the surgeon to vary the orientation and positioning of the end effector at the business end of the instrument. Of course, the mechanisms must be operable at or near the frame of the instrument so that the surgeon can easily manipulate and control these mechanisms while gripping the instrument with his hand.

Often, it may be desirable to rotate the end effector of an endoscopic surgical instrument about the long axis of the shaft of the instrument to vary the orientation of the end effector. Accordingly, many endoscopic surgical instruments include a knob or dial on or adjacent the frame which, when actuated by the surgeon's hand, rotates the shaft of the instrument and correspondingly rotates the end effector.

Another critical feature of certain endoscopic instruments is the ability to pivot the end effector so that the end effector is positioned at an "articulated" position relative to the long axis of the shaft. Consequently, endoscopic instruments often include an articulation knob or dial on or near the frame for remotely articulating the end effector for precise positioning of the end effector within the endoscopic surgical site. Numerous examples of these articulation mechanisms for endoscopic surgical instruments abound. For example, the reader is encouraged to review U.S. Pat. Nos. 4,728,020; 4,869,414; 5,312,023; 5,326,013; 5,330,502; 5,374,277; 5,381,943; 5,383,888; 5,403,342; 5,405,344; 5,409,498; 5,411,519; 5,417,203 and 5,456,684. Articulating mechanisms for pivoting the end effector are also described U.S. Pat. Nos. 5,601,224 and 5,626,587.

Also of interest is U.S. Pat. No. 5,632,432 which describes a mechanism for bending the end effector of an endoscopic instrument through a flexible portion of the shaft.

Although articulating endoscopic surgical instruments are now freely available in commerce and have been described in the literature, the mechanisms which control articulation typically have a significant drawback. When the end effector of the instrument is articulated to a desired position, the end effector is often pushed against the tissue before the end effector is manipulated to perform the desired surgical function. In some cases, the surgeon intentionally uses the articulated end effector to push against the tissue because the surgeon desires to retract or dissect tissue to provide sufficient space within the site for accurately manipulating the end effector to perform the surgical function. Unfortunately, what often occurs when a force is applied to the end effector in an articulated position is that the end effector is forced from its desired articulated position. In other words, the end effector "unwinds" from its desired articulated position, and may shift to another undesired articulated position or revert back to its original, unarticulated position. Obviously, this is a nuisance which would be desirable to overcome.

In addition, when resistance to movement from an articulated position is provided in the articulation assembly to maintain proper positioning (as described in U.S. Pat. No. 5,601,224 discussed above), a corresponding resistance must likewise be provided when the surgeon articulates the end effector to its desired articulated position. In other words, the surgeon must apply a greater force or torque on the articulation knob or dial in order to provide a corresponding increase in the resistance of the end effector to movement from the articulated position.

Furthermore, if too great a force is applied to the end effector in an articulated position, not only may the end effector unwind, but also the components of the articulation assembly may break, leading to a catastrophic failure.

Accordingly, a surgical instrument is needed which characteristically includes an end effector at the business end of the shaft which is capable of being remotely articulated to properly position the end effector. The ability to remotely articulate the end effector is especially important for endoscopic surgical instruments, which characteristically include an elongated cylindrical shaft separating the frame of the instrument from the end effector. Significantly, the mechanism for articulation would desirably resist movement of the end effector in an articulated position when a force is applied to the end effector. Additionally, resistance would be provided without requiring excessive force to position the end effector from an unarticulated to an articulated position. Furthermore, it would be desirable if a fail safe mechanism to prevent component breakage were provided which could reset the articulation assembly if too great a force were applied to the articulated end effector.

SUMMARY OF THE INVENTION

The invention is an articulating surgical instrument having an end effector. The instrument comprises an articulation transmission assembly for remotely articulating the end effector of the instrument. This articulation transmission assembly includes a body, an oscillating member, a rotating member and an actuator. A brief description of these components will now be provided.

The body of the articulation transmission assembly is mounted on the surgical instrument. Extending from the body is a housing.

The oscillating member is seated within the housing of the body for oscillating movement inside the housing. Although oscillating movement inside the housing is provided, the oscillating member is rotationally stationary within the housing. The oscillating member has a first set of unloading teeth and a first set of locking teeth.

The rotating member of the articulation transmission assembly is fitted into the oscillating member for rotational movement within the oscillating member. The rotating member has a drive gear extending into the body of the articulation transmission assembly. The drive gear translates rotational movement of the rotating member into axial movement of at least one elongated transmission band attached to the drive gear. In addition, the rotating member has a second set of locking teeth.

The actuator is rotatably mounted on the housing of the body. It is secured to the rotating member for applying a rotational force on the rotating member. The actuator has a second set of unloading teeth.

When the articulation transmission assembly is in a locked position, the first and second set of locking and unloading teeth are biased towards each other. In this locked position, these teeth are matingly coupled. The coupling of the teeth in combination with the inability of the oscillating member to rotate prevents rotational movement of the rotating member when the articulation transmission assembly is in the locked position.

When the actuator is rotated from the locked position to an unlocked position, the actuator counterbiases the first set of unloading teeth on the oscillating member. Consequently, the first and second set of locking teeth decouple from each other. Therefore, rotational movement of the rotating member is enabled.

The surgical instrument of this invention is capable of providing remote articulation of the end effector of the instrument. It provides articulation transmission in discrete positions to precisely control the degree of articulation. Importantly, the locking and unloading teeth of the oscillating and rotating members of the articulation transmission assembly provide ratcheting rotation to discretely position the end effector. If the end effector is subjected to a high force when in a discrete articulated position, the ratcheting mechanism of the articulation transmission assembly provides a "fail safe" to protect the component parts of the articulation transmission assembly from breakage.

In a particularly preferred embodiment of this invention, each of the teeth from the first and second sets of unloading and locking teeth has a point and a pair of sides diverging from the point. Each of these teeth has a tooth angle defined by a centerline bisecting the tooth from an adjacent tooth and an angled line parallel to one of the pair of sides. Advantageously, the tooth angle for each of the first and second sets of unloading teeth is greater than the tooth angle for each of the first and second sets of locking teeth. Since the tooth angle is greater for the unloading teeth than that for the locking teeth, the rotational resistance between the first and second sets of unloading teeth at the interface between the actuator and the oscillating member is less than the rotational resistance between the first and second sets of locking teeth at the interface between the oscillating and rotating members. Consequently, less rotational force is required to decouple the first and second sets of locking teeth to enable rotational movement of the rotating member when a rotational force is applied to the actuator than the force which would be required when the locking teeth are decoupled independently of a force applied to the actuator.

In other words, when rotational force is applied directly to the end effector in an articulated position, a greater force is necessary to decouple the locking teeth to enable rotational movement to the rotating member because the locking teeth would need to be decoupled independently of the actuator. When the actuator is rotated, the articulation transmission assembly takes advantage of the lower rotational resistance which exists between the unloading teeth to counterbias the first set of unloading teeth on the oscillating member, correspondingly causing the locking teeth to decouple from each other. If the lower rotational resistance is not utilized, then it is necessary to overcome the higher resistance which exists between the first and second sets of locking teeth at the interface between the oscillating and rotating members. In short, the surgeon needs to exert less rotational force to articulate the end effector of the instrument from the articulation transmission assembly than would be required to articulate the end effector by applying a rotational force on the end effector.

The articulating surgical instrument of this invention can be used in any surgical application where it is desired to remotely articulate the end effector of the instrument. The instrument is particularly advantageous for applications involving endoscopic or minimally invasive surgery, but it may also find applications in conventional open surgical procedures as well.

BRIEF DESCRIPTION OF THE DRAWINGS

FIG. 1 is a foreshortened side elevational view of a preferred articulating surgical instrument of this invention in the form of an endoscopic linear stapler. A portion of the frame of the stapler has been truncated to show the attachment of the articulation transmission assembly to the frame.

FIG. 2 is a plan view of the articulating endoscopic linear stapler of FIG. 1 illustrating the articulation of the end effector of the stapler from an unarticulated position.

DETAILED DESCRIPTION OF THE PREFERRED EMBODIMENT

Figure 3:
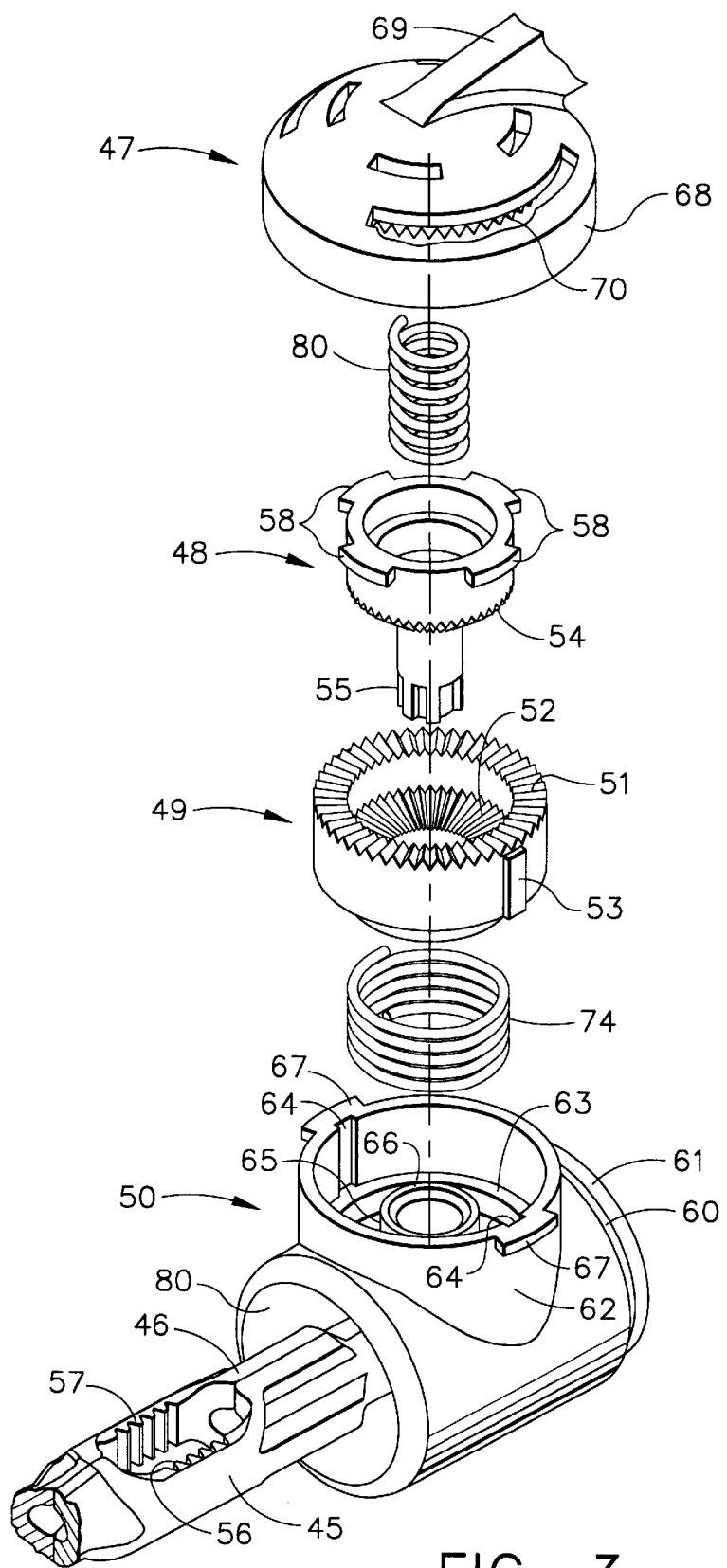
FIG. 3 is an exploded isometric view of the articulation transmission assembly of the endoscopic linear stapler of FIG. 1.

Referring initially to FIG. 1, there is shown the preferred articulating endoscopic stapler 30 of this invention. At a first proximal end 31, the stapler has a frame 32 adapted to enable the user to grip and manipulate the stapler. The frame has a stationary hand grip 33 for placement in the palm of the user's hand, and pivotally mounted clamping and firing triggers, 34 and 35, for remotely clamping tissue and firing staples into the clamped tissue, respectively. At an opposite distal end 36 of the stapler there is the end effector 37 in the form of a surgical fastening assembly. The surgical fastening assembly has an elongated anvil 38 facing an elongated channel 39 adapted to receive a surgical cartridge containing a plurality of staples therein (surgical cartridge not shown). Extending from the frame and coupling the frame to the surgical fastening assembly is an elongated endoscopic shaft 40.

The preferred actuation assembly for the endoscopic stapler 30 to remotely clamp tissue and fire staples into the clamped tissue in response to pivotal counterclockwise rotation of the clamping and firing triggers, 34 and 35, is described U.S. Pat. Nos. 5,465,895 and 5,553,765 each of which are incorporated into this specification by reference. The preferred clamping mechanism within the surgical fastening assembly to urge the anvil from a first position spaced from the elongated channel to a second position adjacent the channel is described in the commonly assigned, co-pending application Ser. No. 08/530,931, filed Sep. 19, 1995, which is also incorporated into this specification by reference.

Referring to FIGS. 1 and 2, the preferred articulating stapler 30 has an articulation transmission assembly 41 coupling the frame 32 with the elongated endoscopic shaft 40 of the stapler. When the articulation transmission assembly is rotated, it causes the remote articulation of the surgical fastening assembly of the stapler. The elongated endoscopic shaft contains a flexible neck 42 enabling the articulation of the surgical fastening assembly to which it is attached. The flexible neck has first and second flexible neck portions, 43 and 44, which receive first and second elongated flexible bands, 45 and 46. Upon rotation of the articulation transmission assembly, one of the first and second flexible transmission bands is moved forwardly and the other band is moved rearwardly. In response to the reciprocating movement of the bands within the first and second flexible portions of the flexible neck, the flexible neck bends to provide articulation. A further description of the flexible neck in an articulating surgical stapler is described in U.S. Pat. No. 5,632,432 which is incorporated by reference into this specification.

The components of the articulation transmission assembly of the preferred endoscopic linear stapler of this invention are illustrated in FIG. 3. The most significant components of the assembly are the actuator 47, rotating cone shaft 48, oscillating cone 49 and nozzle body 50.

Focusing first on the oscillating cone 49, the oscillating cone has a first set of unloading teeth 51 displayed as an outer annular array of teeth. Concentrically displayed internally of the first set of unloading teeth are a first set of locking teeth 52. The oscillating cone also has a pair of anti-rotation lugs 53 (only one lug of the pair of lugs is illustrated in FIG. 3).

The rotating cone shaft 48 is illustrated in further detail when FIG. 3 is taken in combination with FIGS. 10–13. The rotating cone shaft has a second set of locking teeth 54 displayed as an annular array of teeth. When the articulation transmission assembly is assembled, the second set of locking teeth on the rotating cone shaft are positioned in interacting engagement with the first set of locking teeth 52 on the oscillating cone 49. The rotating cone shaft additionally contains four drive lugs 58. It also has an annular upper spring seat 59. Further, the rotating cone shaft has a drive gear 55 which, when the articulation transmission assembly is assembled, descends interiorly into the bore of the nozzle body (a further discussion of the nozzle body is set forth below).

Upon rotation of the rotating cone shaft 48, the drive gear causes reciprocating axial movement of the first and second elongated flexible bands, 45 and 46, through the endoseopic shaft 40 of the stapler. The first and second flexible bands have first and second gear racks, 56 and 57, which couple the bands to the drive gear. Accordingly, when the drive gear is rotated, one of the bands moves forwardly while the other band moves rearwardly. Consequently, the reciprocation of the bands in opposite directions through the first and second flexible neck portions, 43 and 44, of the flexible neck 42 causes the flexible neck of the stapler to bend. In this manner, the articulation of the surgical fastening assembly of the stapler is effected.

Referring now to FIG. 3 in combination with FIGS. 14–18, a further detailed illustration of the nozzle body 50 is provided. The nozzle body has a bore 80 through it to provide continuous communication from the frame 32 of the stapler to the endoscopic shaft 40. The body has a frame groove 60 and a flange 61 to secure the body of the articulation transmission assembly to the frame (see FIG. 1). At the end of the body opposite the flange, the proximal end of the endoscopic shaft of the stapler is frictionally received within the bore. Extending from the nozzle body is a housing 62 to receive the oscillating cone 49 and the rotating cone shaft 48. The housing has an oscillating cone seat 63 and a pair of anti-rotation grooves 64. When the oscillating cone is inserted into the housing, the anti-rotation lugs 53 of the oscillating cone are placed into alignment with the anti-rotation grooves of the housing, and the oscillating cone is therefore seated rotationally stationary on the oscillating cone seat within the housing. Although the oscillating cone is prevented from rotational movement, it may oscillate up and down during operation of the articulation transmission assembly.

The housing 62 extending from the nozzle body 50 also contains an inner tubular post 65 in communication with the bore 80 of the nozzle body. The drive gear 55 of the rotating cone shaft 48 is inserted through the inner tubular post of the housing when the articulation transmission assembly is assembled. The inner tubular post has an annular cone shaft seat 66. Consequently, when the articulation transmission assembly is assembled, the rotating cone shaft is placed into the oscillating cone 49 so that the first and second set of locking teeth interactively engage each other. The oscillating cone is then inserted into the housing with the rotating cone shaft. When inserted, the drive gear is placed through the inner tubular post 65, and the rotating cone shaft sits on the cone shaft seat 66 of the inner tubular post. The oscillating cone is biased in an axial direction away from the oscillating cone seat 63 of the housing and is unable to rotate because of the alignment between the anti-rotation lugs 53 on the cone and the anti-rotation grooves 64 within the housing. In contrast, the rotating cone shaft is capable of rotating within the oscillating cone provided the resistance to rotation created by the coupling of the first and second set of locking teeth can be overcome. Additionally, the housing has a pair of retaining lugs 67 to secure the actuator (discussed below) to the housing.

The actuator 47 is illustrated in detail when the reader refers to FIG. 3 in combination specifically with FIGS. 6–9. The actuator consists of a lever cap 68 and a lever 69 extending from the cap to facilitate the application of a rotational force on the actuator. Within the underside of the lever cap, there is a second set of unloading teeth 70 displayed as an annular array of teeth. The second set of unloading teeth within the cap interact with, and are coupled to, the first set of unloading teeth 52 on the oscillating cone 49 when the articulation transmission assembly is assembled. Interiorly of the second set of unloading teeth, there are four drive lug notches 71. During assembly, the drive lugs 58 of the rotating cone shaft 48 are aligned with the drive lug notches of the lever cap to secure the rotating cone shaft to the cap. The underside of the cap also contains a retaining lip 72 which fits over the retaining lugs on the housing extending from the nozzle body to facilitate the attachment of the lever cap to the housing. Finally, the cap contains four bayonet stops 73 to limit the degree of rotation of the lever cap in either clockwise our counterclockwise directions.

Referring once again to FIG. 3, a lower spring 74 sits within the housing 62 on a lower spring seat 75 and biases the oscillating cone in an upward direction off of oscillating cone seat 63. Correspondingly, an upper spring 81 is secured to the underside of the lever cap and sits against the annular upper spring seat 59 of the rotating cone shaft. Accordingly, the upper spring biases the rotating cone shaft in a downward direction against the cone shaft 66 seat of the inner tubular post 65 of the nozzle body. Consequently, the first and second set of locking teeth are biased toward each other. The upper spring also urges the lever cap 68 in an upward direction so that the retaining lip 72 of the cap resides in frictional contact with the lower surface of the retaining lugs 67 of the nozzle body. Furthermore, pushing down on the lever cap will compress the upper spring, and therefore permit the rotation of the lever cap passed the bayonet stops 73 to facilitate the assembly and disassembly of the articulation transmission assembly.

Figure 4:
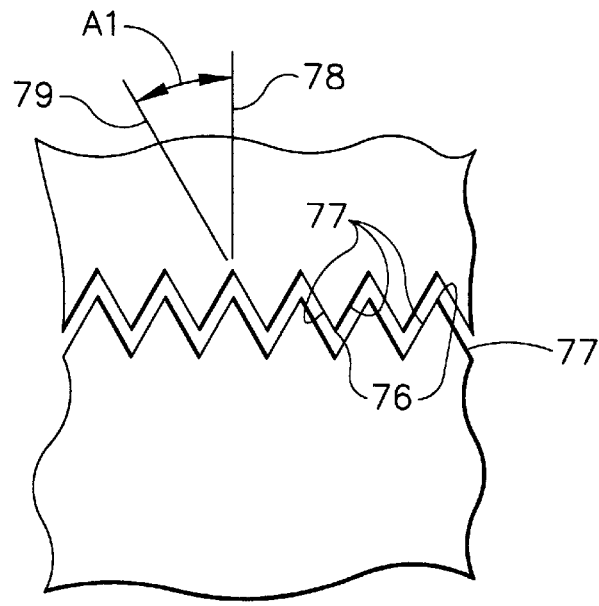
FIG. 4 is a diagrammatic view of the engagement of the first and second set of locking teeth of the articulation transmission assembly shown in FIG. 3.
Figure 5:
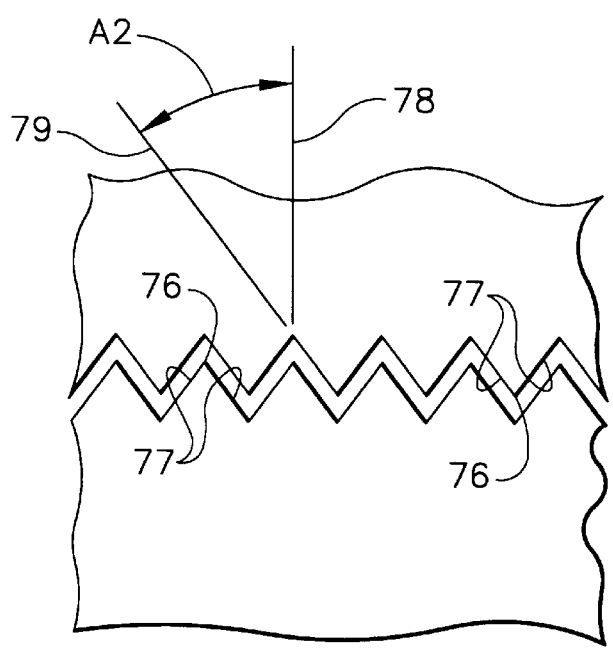
FIG. 5 is a diagrammatic view of the engagement of the first and second set of unloading teeth shown in the articulation transmission assembly shown in FIG. 3.
Figure 6:
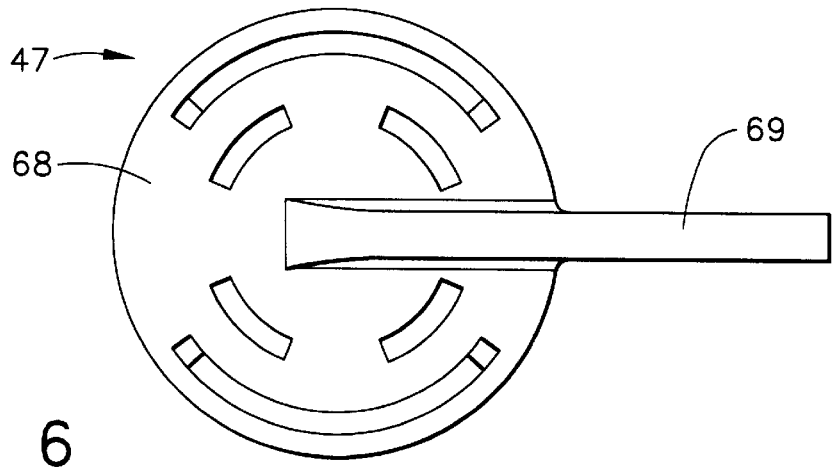
FIG. 6 is a plan view of the actuator of the articulation transmission assembly shown in FIG. 3.
Figure 7:
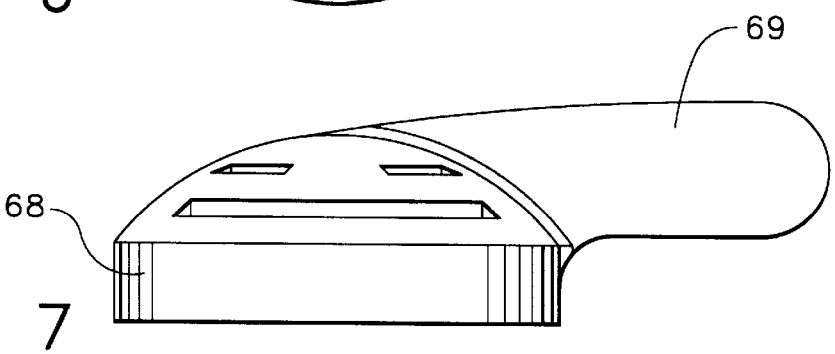
FIG. 7 is a side elevational view of the actuator of FIG. 6.
Figure 8:
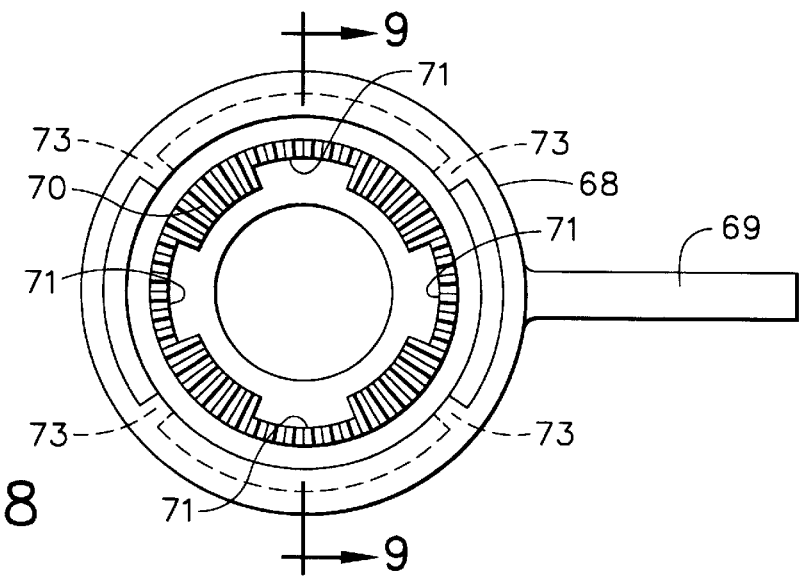
FIG. 8 is a bottom view of the actuator of FIG. 6.
Figure 9:
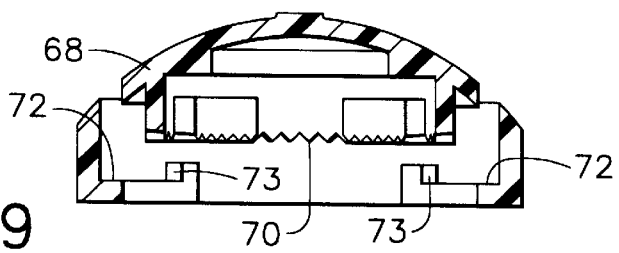
FIG. 9 is a section view taken along line 9—9 of FIG. 8.
Figure 10:
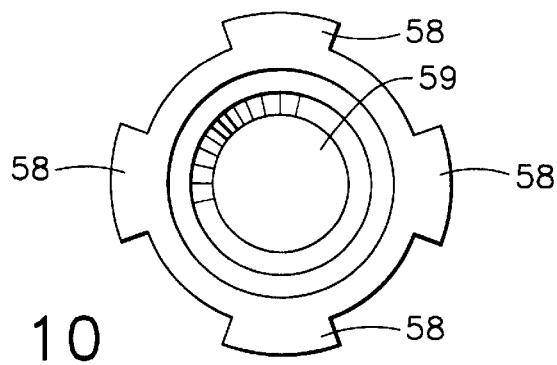
FIG. 10 is a plan view of the rotating member of the articulation transmission assembly shown in FIG. 3.
Figure 11:
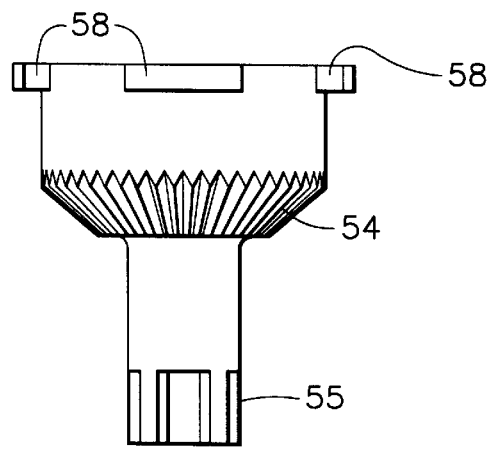
FIG. 11 is a side elevational view of the rotating member of FIG. 10.
Figure 12:
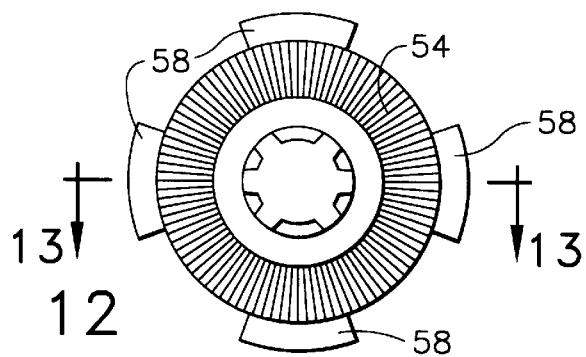
FIG. 12 is a bottom view of the rotating member of FIG. 10.
Figure 13:
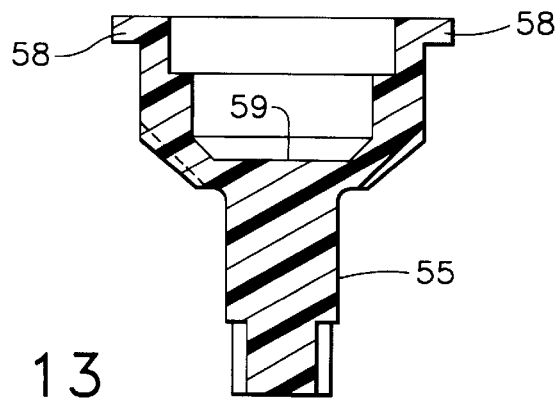
FIG. 13 is a section view taken generally along line 13—13 of FIG. 12.
Figure 14:
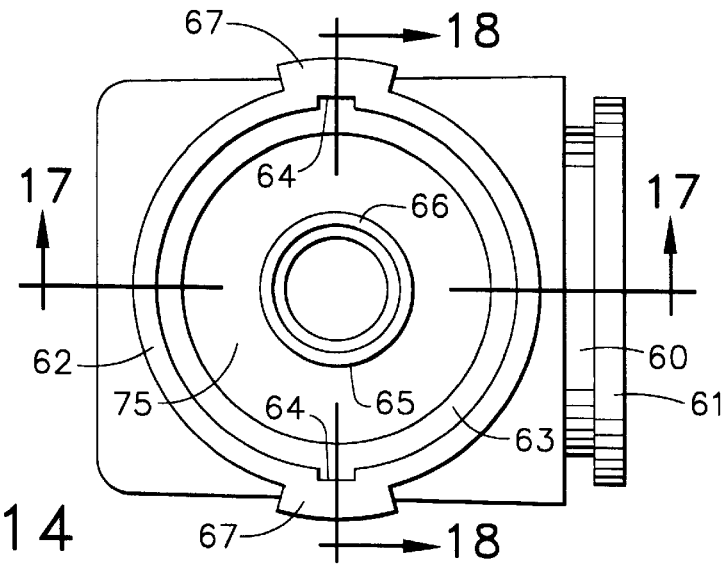
FIG. 14 is a plan view of the body of the articulation transmission assembly shown in FIG. 3.
Figure 15:
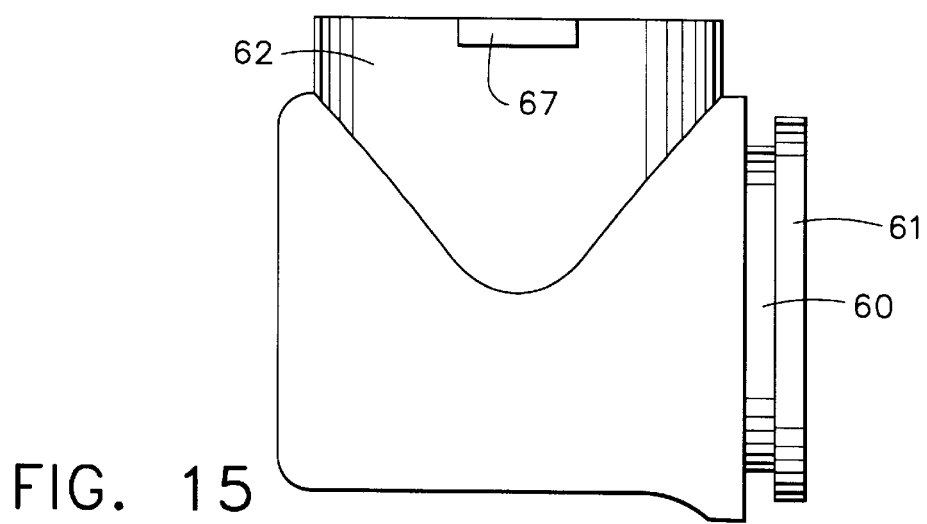
FIG. 15 is a side elevational view of the body of FIG. 14.
Figure 16:
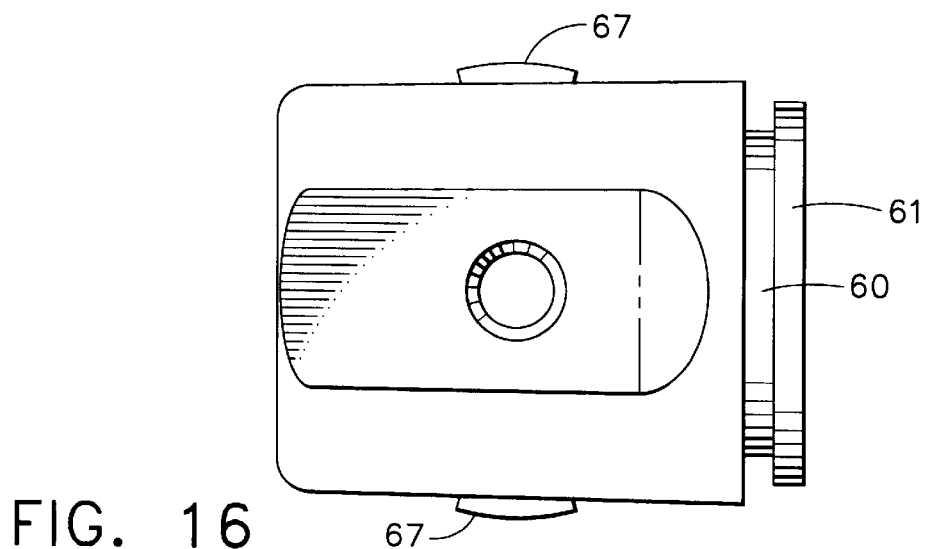
FIG. 16 is a bottom view of the body of FIG. 14.
Figure 17:
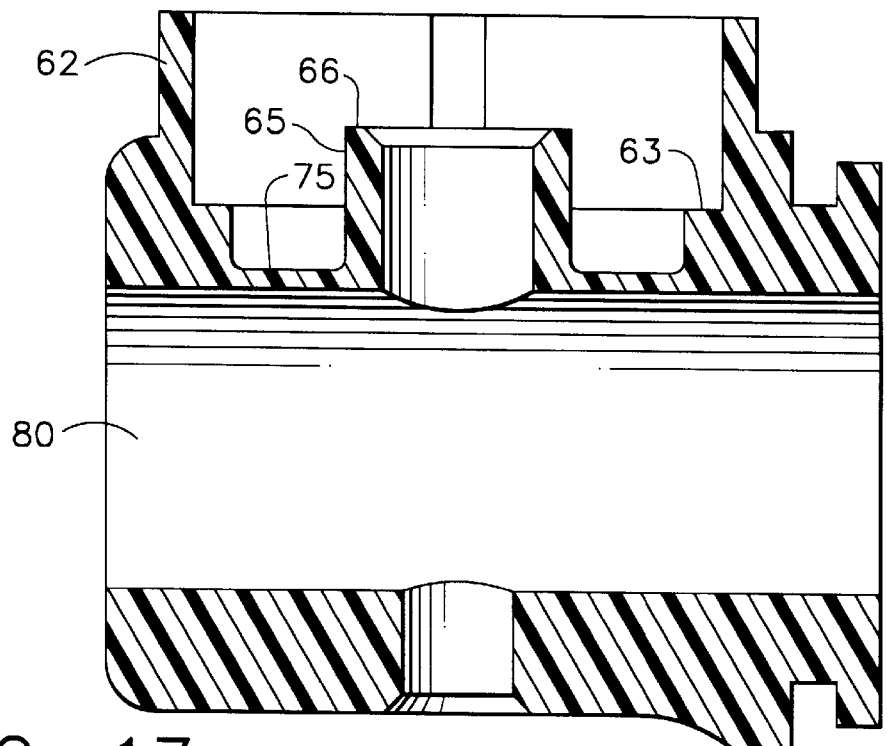
FIG. 17 is a longitudinal section view taken along line 17—17 of FIG. 14.
Figure 18:
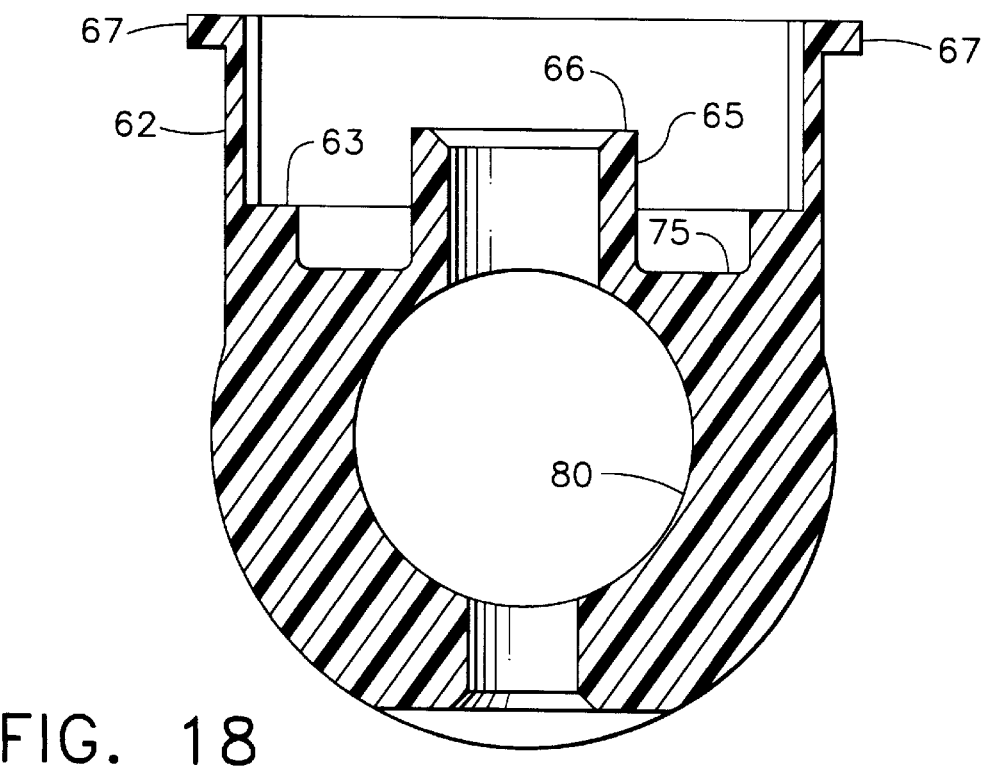
FIG. 18 is a transverse section view taken along line 18—18 of FIG. 14.

Referring now to FIGS. 4 and 5, the reader can observe that each of the first and second sets of locking and unloading teeth in FIGS. 4 and 5, respectively, has a tooth point 76 and a pair of tooth sides 77 diverging from the tooth point. Each tooth has a tooth angle which can be defined by a centerline 78 bisecting the tooth from an adjacent tooth and a line angled from the centerline 79 which is parallel to one of the pair of tooth sides. Advantageously, as illustrated in FIGS. 4 and 5, the tooth angle for each of the first and second sets of unloading teeth, designated as A2 in FIG. 5, is greater than the tooth angle for each of the first and second sets of locking teeth, designated as A1 in FIG. 4. Additionally, the cone shaft, oscillating cone and lever cap are composed of materials which preferably provide a lower coefficient of friction between the first and second sets of unloading teeth than that between the first and second sets of locking teeth. Consequently, the resistance which must be overcome to decouple the first and second sets of locking teeth to effect rotation of the rotating cone shaft is greater than the resistance which must be overcome to decouple the first and second sets of unloading teeth to effect rotation of the lever cap.

Figure 19:
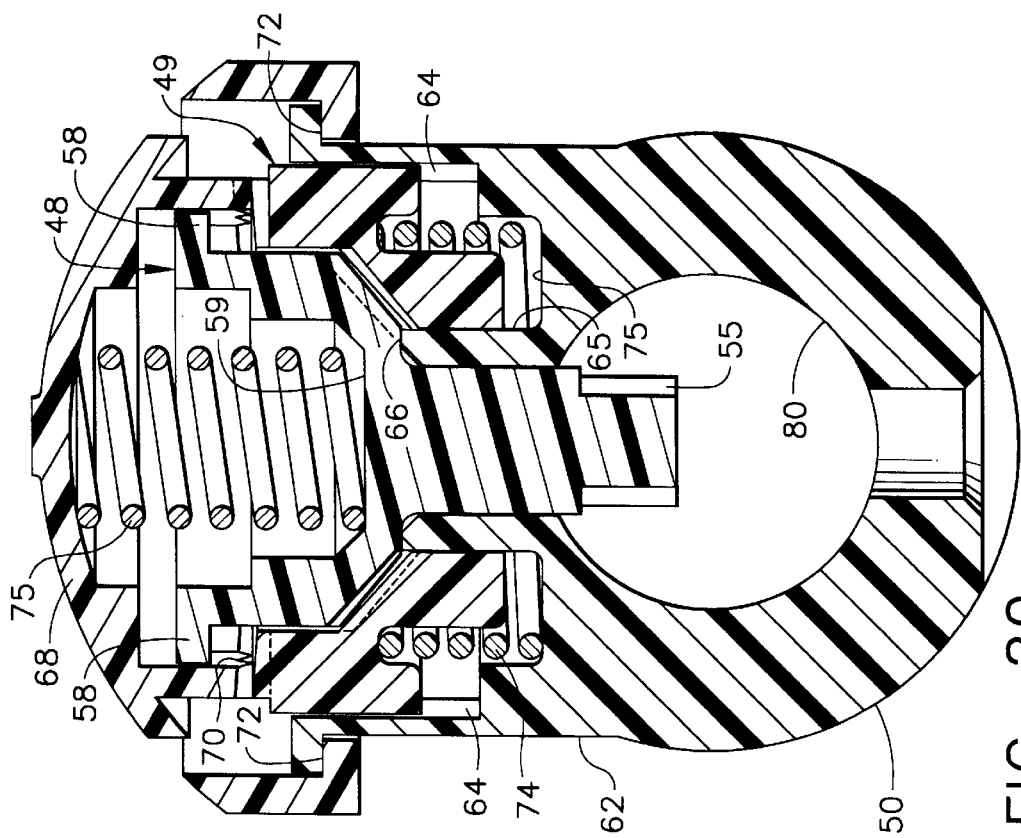
FIG. 19 is an assembly view in the transverse section of the articulation transmission assembly shown in FIG. 3. The assembly is taken along line 19—19 of the locked position, thus locking the end effector of the stapler in a fixed articulation position.

Turning to FIG. 19, the articulation locking assembly is shown in the locked position. In this position, the first and second set of locking and unloading teeth are biased towards each other and matingly coupled to prevent rotation of the lever cap. Therefore, the articulation position of the surgical fastening assembly of the stapler is fixed. If a rotational force were applied directly to the surgical fastening assembly of the stapler, then it becomes necessary to overcome the greater resistance between the first and second sets of locking teeth to effect a change in the articulation position of the surgical fastening assembly.

Figure 20:
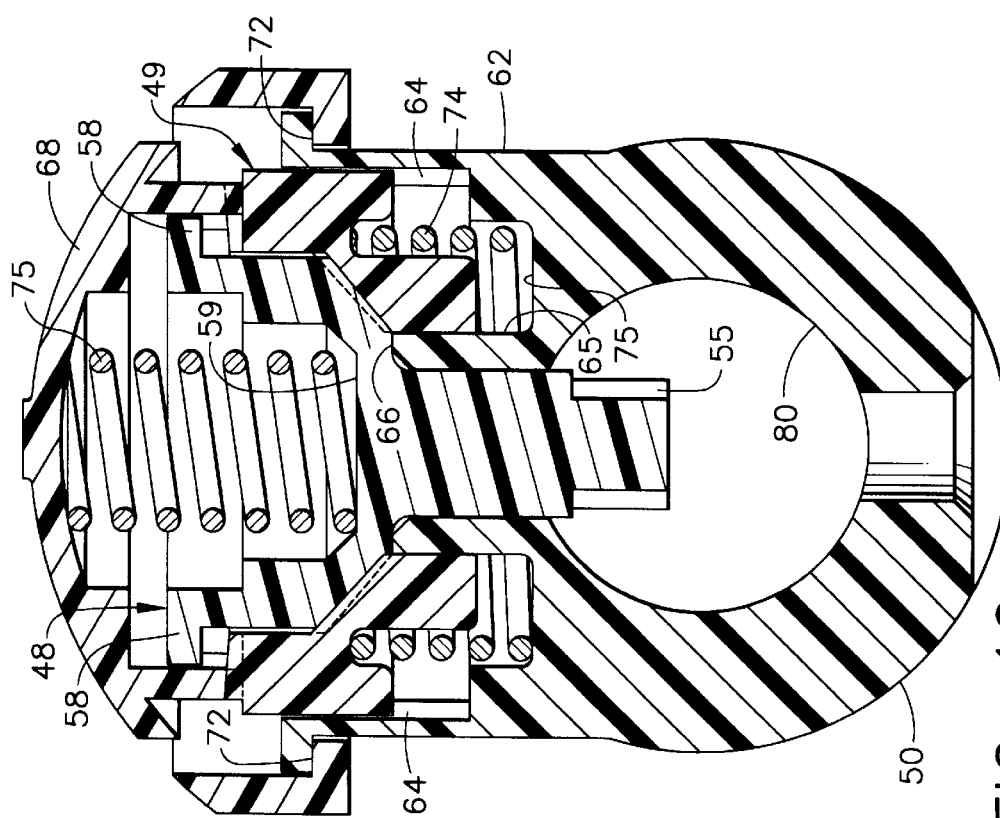
FIG. 20 is another assembly view in transverse section similar to FIG. 19. The assembly is shown in the unlocked position to effect the articulation of the end effector.

In FIG. 20, the articulation transmission assembly is illustrated when a rotational force is applied to the lever. When this rotational force is applied, the ramping action of the second set of unloading teeth within the underside of the lever cap urges the oscillating cone downward since it is prevented from rotational movement (the anti-rotation lugs on the oscillating cone only permit vertical movement of the oscillating cone within the anti-rotation grooves of the housing extending from the nozzle body). Accordingly, the rotational force counterbiases the upward orientation of the oscillating cone created by the lower spring, and causes the first and second sets of unloading teeth to ride over each other as the lever is rotated. Consequently, as the lever is rotated from a locked position to an unlocked position, the first and second sets of locking teeth decouple from each other. Advantageously, the articulation transmission assembly takes advantage of the lower rotational resistance offered by the first and second sets of unloading teeth to facilitate the decoupling of the first and second sets of locking teeth, which independently have a greater rotational resistance.

As the lever is rotated, the articulation transmission assembly causes the remote articulation of the surgical fastening assembly of the stapler. Once the desired degree of articulation is achieved, the rotational force applied to the lever can be released, and the first and second sets of locking and unloading teeth will consequently immediately couple with each other to position the articulation transmission assembly, and therefore the surgical fastening assembly of the stapler, in a locked position.

Although this invention has been described in connection with its most preferred embodiment, numerous additional embodiments will become readily apparent to those skilled in the art. For example, although the invention has been described in connection with an articulating endoscopic stapler, the invention is equally applicable to conventional open surgical instruments. Additionally, although the invention has been described in connection with an articulation transmission assembly which provides for remote articulation of a surgical fastening assembly, it is equally applicable to an instrument which provides remote articulation of a different kind of end effector. Accordingly, the preferred embodiment described in connection with this detailed description is intended to illustrate the invention only, and is not in any way intended to limit the scope or spirit of the claimed invention.

What is claimed is:

1. An articulating surgical instrument (30) having an end effector (37), said instrument comprising an articulation transmission assembly (41) for remotely articulating said end effector of said instrument, said assembly including:
   a) a body (50) mounted on said instrument, said body having a housing (62) extending therefrom;
   b) an oscillating member (49) seated rotationally stationary within said housing for oscillating movement therein, said oscillating member having a first set of unloading teeth (51) thereon and a first set of locking teeth (52) thereon;
   c) a rotating member (48) fitted into said oscillating member for rotational movement therein, said rotating member having a drive gear (55) thereon extending into said body of said articulation transmission assembly for translating rotational movement of said rotating member into axial movement of at least one elongated transmission band (45,46) attached to said drive gear, said rotating member having a second set of locking teeth (54) thereon; and
   d) an actuator (47) rotatably mounted on said housing of said body and secured to said rotating member for applying a rotational force on said rotating member, said actuator having a second set of unloading teeth (70) thereon.

2. The instrument of claim 1 wherein each of said teeth from said first and second sets of unloading and locking teeth has a point (76) and a pair of sides (77) diverging from said point, and each of said teeth has a tooth angle defined by a centerline bisecting said tooth from an adjacent tooth and an angled line parallel to one of said pair of sides, wherein said tooth angle for each of said first and second sets of unloading teeth (A2) is greater than said tooth angle for each of said first and second sets of locking teeth (A1).

3. The instrument of claim 2 wherein when said articulation transmission assembly is in said locked position, a lower spring (74) seated in said housing of said body and an upper spring (81) positioned within said rotating member bias said first and second set of locking and unloading teeth towards each other.

4. The instrument of claim 3 wherein each of said first and second sets of locking and unloading teeth is displayed as a ring of said teeth.

5. The instrument of claim 4 wherein said first and second sets of locking teeth are concentrically displayed between said first and second sets of unloading teeth.

6. The instrument of claim 5 wherein said actuator has a cap (68) rotatably mounted on said housing, and a lever (69) extending from said cap for gripping said actuator so as to apply a rotational force thereon.

7. The instrument of claim 6 wherein said cap contains said second set of unloading teeth thereon.

8. The instrument of claim 2 wherein said first and second sets of unloading teeth have a first coefficient of friction, said first and second sets of locking teeth have a second coefficient of friction, and said first coefficient of friction is less than said second coefficient of friction.

9. The instrument of claim 1 wherein said at least one elongated transmission band is a flexible band.

* * * * *